US010716459B2

(12) United States Patent
Sakai et al.

(10) Patent No.: US 10,716,459 B2
(45) Date of Patent: Jul. 21, 2020

(54) ENDOSCOPE SYSTEM AND ENDOSCOPE

(71) Applicant: OLYMPUS CORPORATION, Tokyo (JP)

(72) Inventors: Aiko Sakai, Kodaira (JP); Hideyuki Kugimiya, Hachioji (JP); Ryo Koshida, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 325 days.

(21) Appl. No.: 15/706,678

(22) Filed: Sep. 16, 2017

(65) Prior Publication Data

US 2018/0014716 A1 Jan. 18, 2018

Related U.S. Application Data

(63) Continuation of application No. PCT/JP2016/077265, filed on Sep. 15, 2016.

(30) Foreign Application Priority Data

Mar. 7, 2016 (JP) .................................. 2016-043617

(51) Int. Cl.
*A61B 1/00* (2006.01)
*A61B 1/05* (2006.01)
*H04N 5/225* (2006.01)

(52) U.S. Cl.
CPC ...... *A61B 1/00013* (2013.01); *A61B 1/00009* (2013.01); *A61B 1/00018* (2013.01);
(Continued)

(58) Field of Classification Search
CPC ............ A61B 1/00009; A61B 1/00013; A61B 1/00018; A61B 1/05; A61B 1/00059; H04N 2005/2255

See application file for complete search history.

(56) References Cited

U.S. PATENT DOCUMENTS 4,473,841 A * 9/1984 Murakoshi ......... A61B 1/00013
128/901
6,458,078 B1 * 10/2002 Ludtke ............... A61B 1/00013
348/E5.029
(Continued)

FOREIGN PATENT DOCUMENTS

CN 103002790 A 3/2013
CN 105163646 A 12/2015
(Continued)

OTHER PUBLICATIONS

Japanese Office Action dated Apr. 18, 2017 received in 2016-576001.

*Primary Examiner* — Aaron B Fairchild
(74) *Attorney, Agent, or Firm* — Scully, Scott, Murphy & Presser, P.C.

(57) ABSTRACT

An endoscope system includes: an image pickup device configured to output a digital signal; an EEPROM in which predetermined information concerning an endoscope is recorded; a signal control portion capable of selectively converting data of one of the digital signal outputted from the image pickup device and the predetermined information of the EEPROM to serial data and outputting the serial data; an electro-optical conversion portion configured to convert the data outputted from the signal control portion to an optical signal and output the optical signal; a universal cable; and a data switching portion switched to transfer the predetermined information from the EEPROM by the signal control portion and then transfer the digital signal by the signal control portion. The signal control portion decides through which of a metal transmitting member and an optical transmitting member the predetermined information is transmitted, based on a data amount of the predetermined information.

10 Claims, 4 Drawing Sheets

(52) U.S. Cl.
CPC ............ *A61B 1/00059* (2013.01); *A61B 1/05* (2013.01); *A61B 1/0002* (2013.01); *A61B 1/00006* (2013.01); *A61B 1/00121* (2013.01); *H04N 2005/2255* (2013.01)

(56) References Cited

U.S. PATENT DOCUMENTS

| | | | |
|---|---|---|---|
| 9,198,557 B2* | 12/2015 | Takizawa | A61B 1/00006 |
| 9,439,554 B2* | 9/2016 | Usami | A61B 1/00004 |
| 2008/0039686 A1* | 2/2008 | Mori | A61B 1/00165 |
| | | | 600/109 |
| 2010/0130820 A1 | 5/2010 | Shigemori et al. | |
| 2012/0320176 A1* | 12/2012 | Tanaka | A61B 1/00006 |
| | | | 348/65 |
| 2013/0096380 A1 | 4/2013 | Matsuzawa et al. | |
| 2013/0123578 A1 | 5/2013 | Gocho et al. | |
| 2013/0141557 A1 | 6/2013 | Kawata et al. | |
| 2013/0169775 A1* | 7/2013 | Ono | A61B 1/00009 |
| | | | 348/68 |
| 2013/0235175 A1* | 9/2013 | Kazama | H04N 7/18 |
| | | | 348/65 |
| 2016/0029874 A1* | 2/2016 | Usami | A61B 1/00004 |
| | | | 600/110 |
| 2016/0206185 A1* | 7/2016 | Kinouchi | A61B 1/04 |
| 2016/0316995 A1* | 11/2016 | Michihata | A61B 1/00006 |
| 2016/0323539 A1* | 11/2016 | Michihata | H04N 17/004 |
| 2017/0095137 A1* | 4/2017 | Kinouchi | A61B 1/04 |
| 2017/0202432 A1* | 7/2017 | Michihata | A61B 1/00055 |
| 2017/0202435 A1* | 7/2017 | Michihata | A61B 1/00018 |
| 2017/0206624 A1* | 7/2017 | Michihata | A61B 1/00009 |
| 2017/0272665 A1* | 9/2017 | Kugimiya | A61B 1/00004 |
| 2017/0280982 A1* | 10/2017 | Kugimiya | A61B 1/04 |
| 2017/0303771 A1* | 10/2017 | Sudo | A61B 1/00057 |
| 2019/0246033 A1* | 8/2019 | Yamamoto | H04N 5/2254 |
| 2019/0246875 A1* | 8/2019 | Mizoguchi | G02B 23/2415 |

FOREIGN PATENT DOCUMENTS

| | | |
|---|---|---|
| EP | 2 174 581 A1 | 4/2010 |
| EP | 2 626 000 A1 | 8/2013 |
| EP | 2 626 002 A1 | 8/2013 |
| EP | 2 987 449 A1 | 2/2016 |
| JP | 2009-28081 A | 2/2009 |
| WO | 2012/046856 A1 | 4/2012 |
| WO | 2012/132096 A1 | 10/2012 |
| WO | 2014/171332 A1 | 10/2014 |

* cited by examiner

ENDOSCOPE SYSTEM AND ENDOSCOPE

CROSS REFERENCE TO RELATED APPLICATION

This application is a continuation application of PCT/JP2016/077265 filed on Sep. 15, 2016 and claims benefit of Japanese Application No. 2016-043617 filed in Japan on Mar. 7, 2016, the entire contents of which are incorporated herein by this reference.

BACKGROUND OF THE INVENTION

1. Field of the Invention

The present invention relates to an endoscope system and an endoscope, and in particular relates to an endoscope system and an endoscope capable of transmitting an image signal by an optical transmitting member.

2. Description of the Related Art

An endoscope has been widely utilized in a medical field and an industrial field. The endoscope displays an image of an object acquired through an observation window at a distal end of an insertion portion at a display apparatus as an endoscopic image, and is used for an inspection or the like.

An object image is photoelectrically converted in an image pickup device, and an image pickup signal is outputted from the endoscope through wires as an image signal.

In addition, in recent years, as a number of pixels of the image pickup device increases, a technique of transmitting the image signal by an optical fiber which is an optical transmitting member has been proposed.

Since the optical fiber is weak against bending stress and is easily damaged or disconnected, in order to be able to continue observation of an object by an endoscope even when there is such damage or the like, an endoscope system including two kinds of transmission means for transmission by an optical signal and transmission by an electric signal is proposed and disclosed in International Publication No. WO2012/046856.

Further, International Publication No. WO2014/171332 proposes and discloses an endoscope system in which a processor receives identification information from a connected object and switches a transmission line for reception based on the identification information so as to cope with both of an endoscope capable of transmitting only an electric signal and an endoscope capable of transmitting only an optical signal.

SUMMARY OF THE INVENTION

An endoscope system of one aspect of the present invention includes: an image pickup portion configured to pick up an image inside a subject and output a digital signal; a recording portion in which predetermined information concerning an endoscope is recorded; a signal control portion capable of selectively converting data of one of the digital signal outputted from the image pickup portion and the information from the recording portion to serial data and outputting the serial data; an electro-optical conversion portion configured to convert the data outputted from the signal control portion to an optical signal and output the optical signal; a cable configured by an optical transmitting member configured to transmit the optical signal outputted from the electro-optical conversion portion and a metal transmitting member configured to transmit the data outputted from the signal control portion; and a data switching portion switched to transfer the predetermined information from the recording portion by the signal control portion and then transfer the digital signal by the signal control portion, and the signal control portion decides through which of the metal transmitting member and the optical transmitting member the predetermined information is transmitted, based on a data amount of the predetermined information.

An endoscope of one aspect of the present invention includes: an image pickup portion configured to pick up an image inside a subject and output a digital signal; a recording portion in which predetermined information concerning the endoscope is recorded; a signal control portion capable of selectively converting data of one of the digital signal outputted from the image pickup portion and the predetermined information in the recording portion to serial data and outputting the serial data; an electro-optical conversion portion configured to convert the data outputted from the signal control portion to an optical signal and output the optical signal; and a data switching portion switched to transfer the predetermined information from the recording portion by the signal control portion and then transfer the digital signal to the signal control portion, and the signal control portion decides through which of a metal transmitting member and an optical transmitting member the predetermined information is transmitted, based on a data amount of the predetermined information.

DETAILED DESCRIPTION OF THE PREFERRED EMBODIMENT(S)

Hereinafter, an embodiment of the present invention will be described with reference to the drawings.

Figure 1:
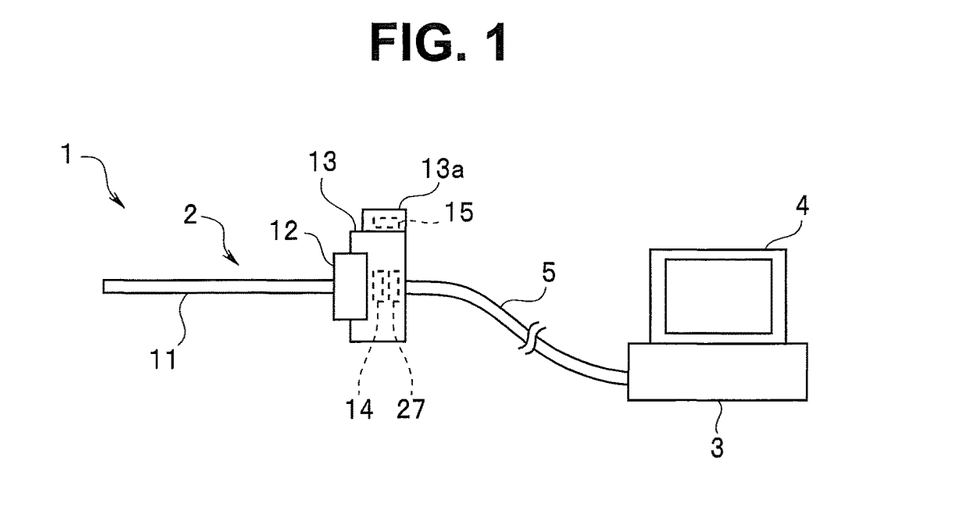
FIG. 1 is a configuration diagram of an endoscope system relating to an embodiment of the present invention.

FIG. 1 is a configuration diagram of an endoscope system relating to the present embodiment. An endoscope system 1 is configured including an endoscope 2, a video processor 3, and a display apparatus 4. The endoscope 2 and the video processor 3 are connected by a universal cable 5.

The endoscope 2 is a rigid endoscope, and includes an insertion portion 11, an eyepiece portion 12, and a camera head 13.

The insertion portion 11 includes an objective lens system and a relay lens system arranged inside a rigid tubular member. The eyepiece portion 12 is provided on a proximal end portion of the insertion portion 11. The eyepiece portion 12 includes an eyepiece lens, and an operator can view an image of an object by bringing eyes closer to the eyepiece portion 12.

Further, the endoscope 2 includes the camera head 13 detachably mounted on the eyepiece portion 12.

The camera head 13 incorporates an image pickup device 14. The image pickup device 14 includes an image pickup surface that receives light which has passed through the eyepiece lens of the eyepiece portion 12. The image pickup device 14 outputs an image signal having for example a 4K resolution or an 8K resolution, here.

Further, the camera head 13 is provided with an operation portion 13a including various kinds of switches such as a freeze button, that a user can operate.

The video processor 3 is a processor configured to execute various kinds of image processing on the image signal received from the endoscope 2 and output the image signal to the display apparatus 4. The display apparatus 4 receives the image signal and displays an endoscopic image.

The universal cable 5 includes a plurality (two, here) of optical fibers that are optical transmitting members, and the image signal including pixel information obtained in the image pickup device 14 is transmitted from the camera head 13 to the video processor 3 by the optical signal through the plurality of optical fibers.

Note that the eyepiece portion 12 and the camera head 13 are separate here. However, the eyepiece portion 12 and the camera head 13 may be united so as to be inseparable.

For the endoscopic image, since the number of pixels is large, an image of one frame is divided into a plurality of pixel areas, and the endoscope 2 transmits the image signal of each pixel area through the universal cable 5 to the video processor 3.

Figure 2:
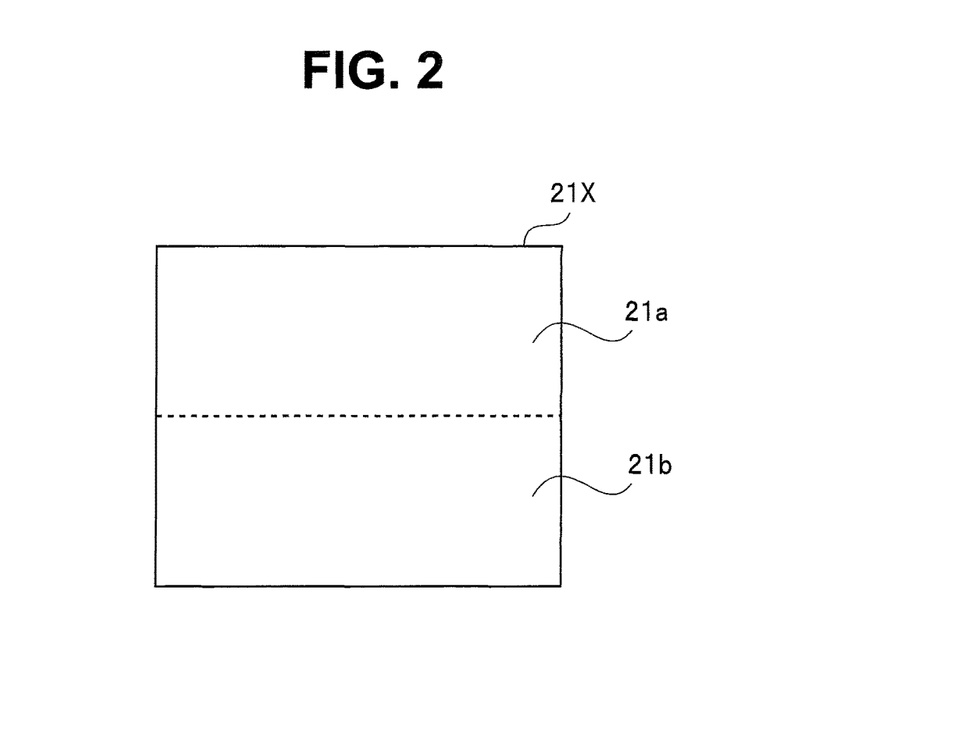
FIG. 2 is a diagram for describing division of an endoscopic image relating to the embodiment of the present invention.

FIG. 2 is a diagram for describing division of the endoscopic image. FIG. 2 illustrates that an endoscopic image 21X is divided into a plurality, two in this case.

More specifically, the endoscopic image 21X of one frame is divided into two pixel areas 21a and 21b. The image signals of the respective pixel areas include a plurality of pieces of pixel information within the pixel area and are transmitted in parallel to the video processor 3.

Figure 3:
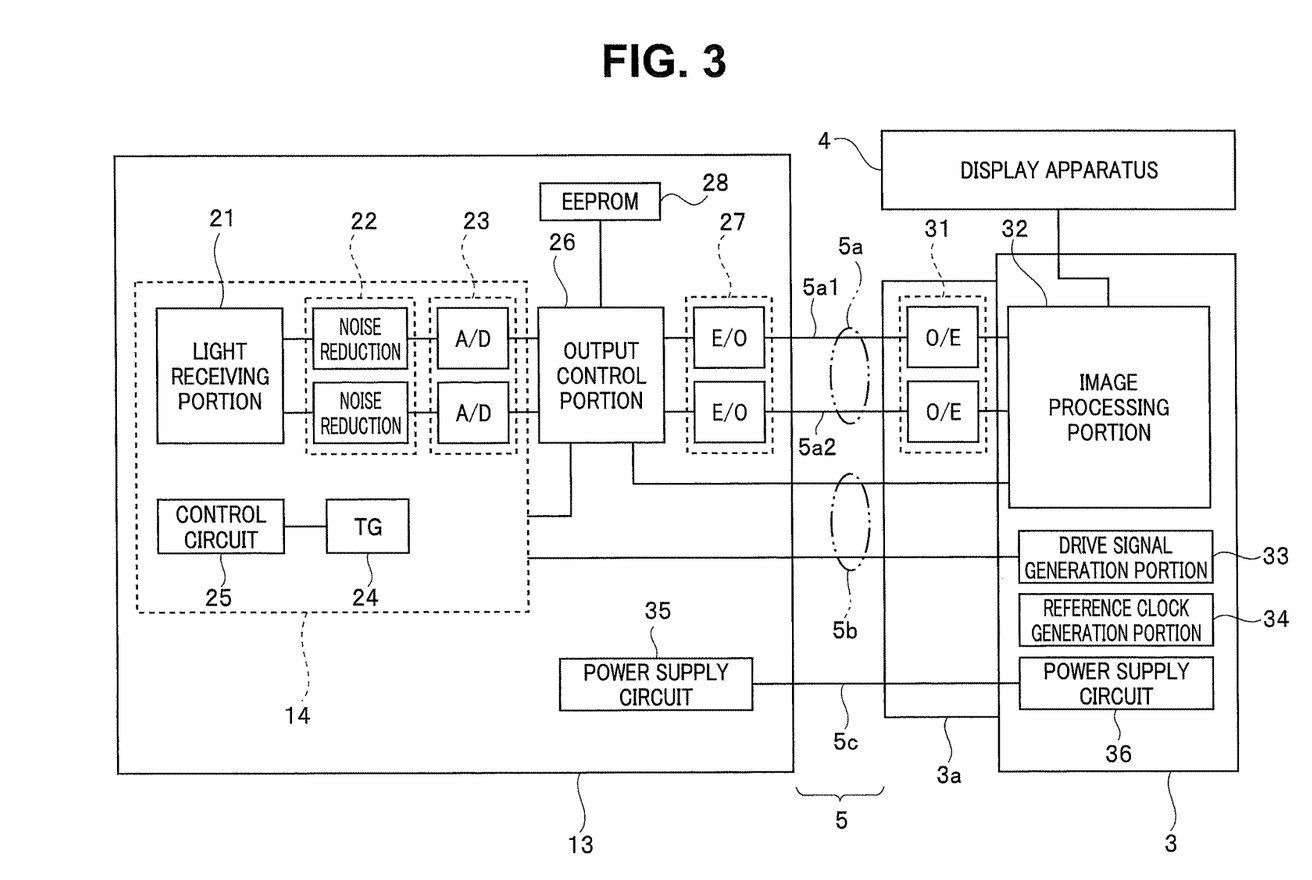
FIG. 3 is a block diagram illustrating a configuration of an endoscope system 1 relating to the embodiment of the present invention.

FIG. 3 is a block diagram illustrating the configuration of the endoscope system 1.

The universal cable 5 is connected to the camera head 13, and the universal cable 5 extending from the camera head 13 is connected to the video processor 3 through a connector 3a. Into the universal cable 5, a plurality of optical fibers 5a and a plurality of electric wires 5b are inserted. The plurality of wires 5b include metal transmitting members such as metal conductors, and configure, as described later, a metal transmission portion for transmitting various kinds of information.

Note that the plurality of optical fibers arranged in the universal cable 5 are formed into an extremely narrow diameter (for example, a diameter of 0.125 mm) with quartz glass for example and are very fragile, so that each optical fiber is protected by being primarily coated with an ultraviolet curing type resin for example and then further coated with a protective tube for example. At the time, the plurality of primarily coated optical fibers may be put together and coated with the protective tube, or each of the plurality of primarily coated optical fibers may be individually coated with the protective tube.

In addition, the metal transmitting members arranged in the universal cable 5 may also be coated with the protective tube respectively, or two or more may be turned to an insulated state and then put together to be protected with the protective tube for example.

Then, the plurality of optical fibers and metal transmitting members may be appropriately arranged inside the universal cable 5. However, it is better to be symmetrical to a cable center axis for example. When an arrangement symmetrical to the cable center axis is adopted, the universal cable 5 can be bent in an arbitrary direction by the same curvature. A situation where it is easy to bend in a specific direction but difficult to bend in another specific direction does not occur. Therefore, the universal cable 5 can be easily handled.

Examples of the arrangement symmetrical to the cable center axis are symmetrically arranging the metal transmitting members so as to surround the plurality of optical fibers that are put together as an axial center, or symmetrically arranging the plurality of optical fibers so as to surround metal wires that are put together as the axial center. No matter what arrangement is adopted, the metal transmitting members can achieve a function as a tension member that protects the optical fibers from tension applied to the universal cable 5.

The image pickup device 14 inside the camera head 13 is a CMOS image sensor, and includes a light receiving portion 21 including a light receiving surface, a noise reduction portion 22, an analog/digital conversion portion (abbreviated as A/D, hereinafter) 23, a timing generator (abbreviated as TG, hereinafter) 24, and a control circuit 25.

The image pickup device 14 is a CMOS image pickup device, and the light receiving surface of the light receiving portion 21 is divided into the two pixel areas 21a and 21b. The image signal photoelectrically converted in the light receiving portion 21 is outputted to the noise reduction portion 22.

More specifically, the image signals of the two pixel areas 21a and 21b are respectively outputted to two noise reduction circuits inside the noise reduction portion 22. The noise reduction portion 22 outputs the noise-reduced image signal of each pixel area to the A/D 23.

Therefore, the image pickup device 14 configures an image pickup portion that picks up an image inside a subject and outputs two or more digital signals, the digital signals of the two pixel areas in this case. In the present embodiment, the image pickup device 14 is divided into two pixel areas. However, the image pickup device 14 may be divided into three or more pixel areas. The two or more digital signals outputted from the image pickup device 14 correspond to two or more divided image pickup areas of the image obtained by picking up the image of the object.

The A/D 23 includes analog/digital conversion circuits for the respective pixel areas, converts the image signal from an analog signal to a digital signal, and outputs the digital signal to an output control portion 26. In FIG. 3, output of each analog/digital conversion circuit of the A/D 23 is illustrated by one line. However, the image signal outputted from each analog/digital conversion circuit is a parallel signal.

The TG 24 generates various kinds of timing signals and outputs the timing signals to the control circuit 25. The control circuit 25 drives the light receiving portion 21, the noise reduction portion 22 and the A/D 23, based on the various kinds of timing signals.

The camera head 13 includes the output control portion 26, an electro-optical conversion portion 27 and an EEPROM 28, in addition to the image pickup device 14.

The output control portion 26 outputs the image signals from the A/D 23 to the electro-optical conversion portion 27 and also reads data in the EEPROM 28 and outputs the data to the video processor 3. The configuration of the output control portion 26 will be described later.

The electro-optical conversion portion 27 is provided inside the camera head 13. The electro-optical conversion portion 27 includes two electro-optical converters (E/O) corresponding to the two image signals from the output control portion 26. The two electro-optical converters are respectively connected with two optical fibers 5a1 and 5a2 inserted into the universal cable 5.

That is, the electro-optical conversion portion 27 includes the plurality of electro-optical converters, converts the plurality (two, here) of digital signals outputted from the image pickup device 14 to the optical signals and outputs the optical signals in parallel from the plurality (two, here) of electro-optical converters. The plurality of optical fibers 5a configure an optical transmission portion that includes the plurality (two, here) of optical transmitting members and is adapted to transmit the plurality (two, here) of optical signals outputted from the electro-optical conversion portion 27 in parallel by the plurality (two, here) of optical transmitting members.

In the EEPROM 28, identification information (referred to as ID, hereinafter) of the camera head 13 or the like is stored. The EEPROM 28 is a rewritable nonvolatile memory.

In the EEPROM 28, not only the ID but also various kinds of information concerning image and information on an image processing program (referred to as image processing information, hereinafter) is sometimes stored. That is, the EEPROM 28 configures a recording portion in which predetermined information concerning the endoscope 2 is recorded.

The ID is endoscope scope information and a serial number of the camera head or the like.

The various kinds of information include defective pixel information of the image pickup device 14, white balance information, color variation correction information and an adjustment parameter.

The image processing program is a program of the image processing executed to the image signals outputted from the camera head 13. The image processing program is sent from the camera head 13 to the video processor 3, and the video processor 3 uses the received image processing program to execute the image processing on the image signals from the camera head 13.

Note that, here, the output control portion 26 and the EEPROM 28 are loaded on a circuit board 15 provided inside the operation portion 13a for example.

As above, inside the camera head 13, the image pickup device 14, the output control portion 26, the electro-optical conversion portion 27 and the EEPROM 28 are provided. Then, the plurality (two, here) of optical fibers that are the optical transmitting members are provided in parallel corresponding to the number of the image signals outputted from the image pickup device 14 inside the universal cable 5.

The connector 3a is provided with an opto-electrical conversion portion 31.

The opto-electrical conversion portion 31 includes two opto-electrical conversion circuits (O/E) corresponding to the two optical fibers 5a1 and 5a2. That is, the opto-electrical conversion portion 31 is provided around the connector 3a at an end portion of the universal cable 5, and converts the optical signals transmitted by the plurality of optical fibers 5a which is the optical transmission portion to electric signals.

The video processor 3 includes an image processing portion 32, a drive signal generation portion 33, and a reference clock generation portion 34.

The image processing portion 32 combines the image signals received through the opto-electrical conversion portion 31, executes predetermined image processing on the received image signals based on the received image processing information, and generates the endoscopic image. The image signals of the generated endoscopic image are supplied to the display apparatus 4, and the endoscopic image is displayed on a display screen.

For example, in a case where the image processing portion 32 includes a plurality of image processing programs or circuits according to kinds of the endoscope or the like and the image processing according to the received ID (image processing information), color adjustment processing for example, is determined, the image processing portion 32 selects the image processing program or circuit according to the ID, and executes appropriate processing on the received image signals. Further, the image processing portion 32 sometimes executes the image processing using the received information (image processing information) such as the defective pixel information to the received image signals. In addition, the image processing portion 32 sometimes executes the image processing by the received image processing program (image processing information) to the received image signals.

The drive signal generation portion 33 generates a drive signal that drives various kinds of circuits inside the image pickup device 14, and supplies the drive signal to the camera head 13 through some of the plurality of wires 5b.

The reference clock generation portion 34 generates a reference clock to be a reference of timing to drive the various kinds of circuits inside the video processor 3.

Note that the drive signal generation portion 33 and the reference clock generation portion 34 are provided inside the video processor 3 here, but may be provided inside the camera head 13.

The camera head 13 and the video processor 3 include power supply circuits 35 and 36 as power supply portions respectively. The power supply circuits 35 and 36 are connected through a power supply line 5c inserted into the universal cable 5.

Figure 4:
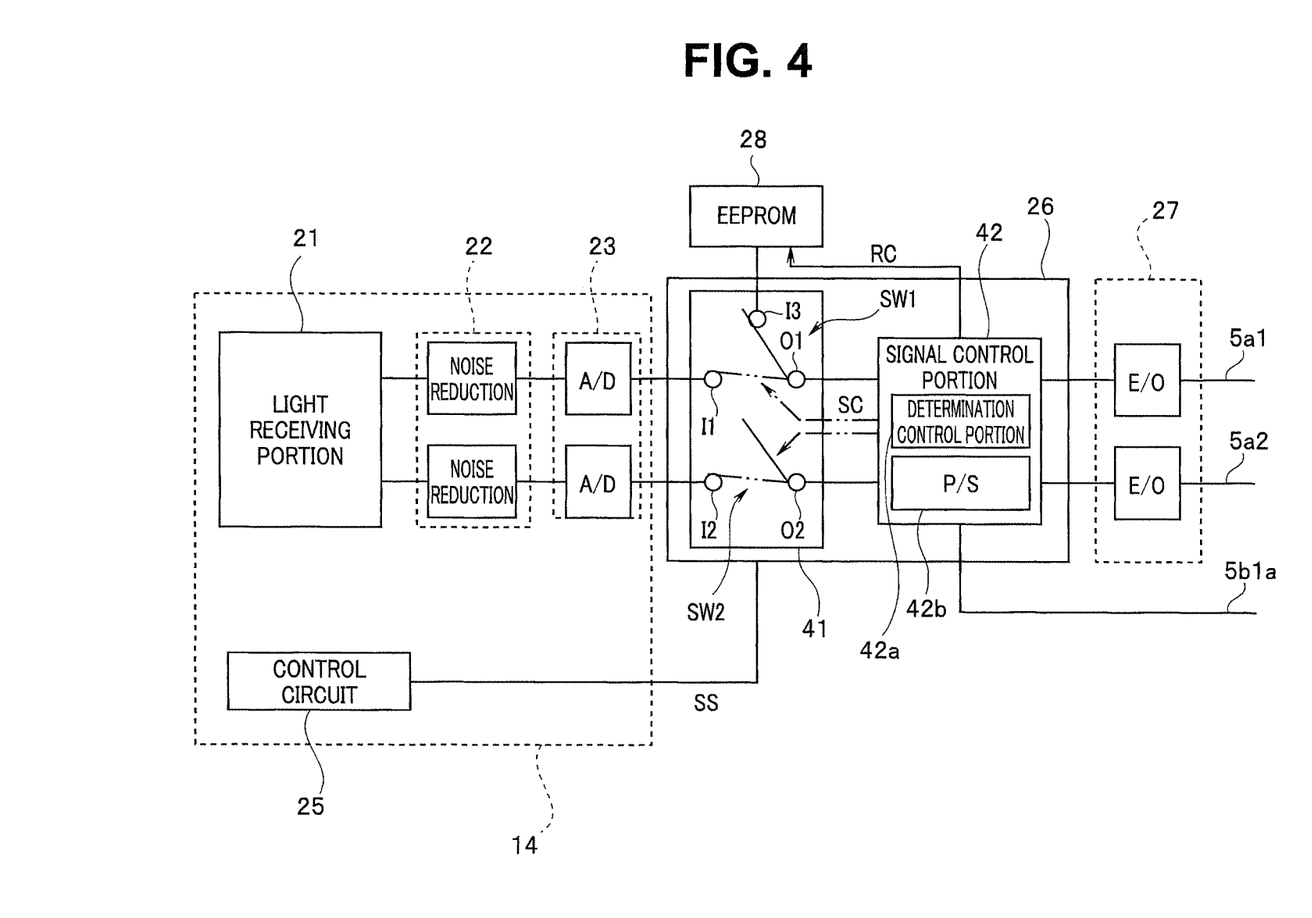
FIG. 4 is a diagram for describing a configuration of an output control portion 26 relating to the embodiment of the present invention.

FIG. 4 is a diagram for describing the configuration of the output control portion 26.

The output control portion 26 includes a data switching portion 41 and a signal control portion 42.

The data switching portion 41 includes a plurality (two, here) of input ends connected to the A/D 23, an input end connected to the EEPROM 28, a plurality (two, here) of output ends connected to the signal control portion 42, and an output end connected to a wire 5b1a of the plurality of wires.

More specifically, the data switching portion 41 includes two switches SW1 and SW2. The data switching portion 41 includes three input ends. One input end I1 is connected to one analog/digital conversion circuit of the A/D 23, one input end I2 is connected to the other analog/digital conversion circuit of the A/D 23, and the other input end I3 is connected to the EEPROM 28. The data switching portion 41 includes two output ends O1 and O2. The two output ends O1 and O2 are connectable to the two electro-optical converters of the E/O 27 respectively through the signal control portion 42.

The switch SW1 includes the two input ends I1 and I3 and the output end O1, and the output end of the switch SW1 is selectively connectable to either one of the two input ends I1 and I3, based on a control signal SC.

The switch SW2 includes the one input end I2 and the output end O2, and the output end of the switch SW2 is selectively connectable to the input end I2, based on the control signal SC.

That is, in the data switching portion 41, since the switches SW1 and SW2 are switched based on the control signal SC from the signal control portion 42, a connection state of respective input terminals and a plurality of output terminals is switched.

The signal control portion 42 includes a determination control portion 42a and a parallel/serial conversion portion (abbreviated as P/S, hereinafter) 42b.

The determination control portion 42a is a circuit that determines whether or not a data amount of the information read from the EEPROM 28 is equal to or larger than a predetermined threshold TH, and controls switching of the two switches SW1 and SW2 of the data switching portion 41.

The P/S 42b converts parallel signals outputted from the two output terminals of the data switching portion 41 to serial signals and outputs the serial signals to the electro-optical conversion portion 27.

Figure 5:
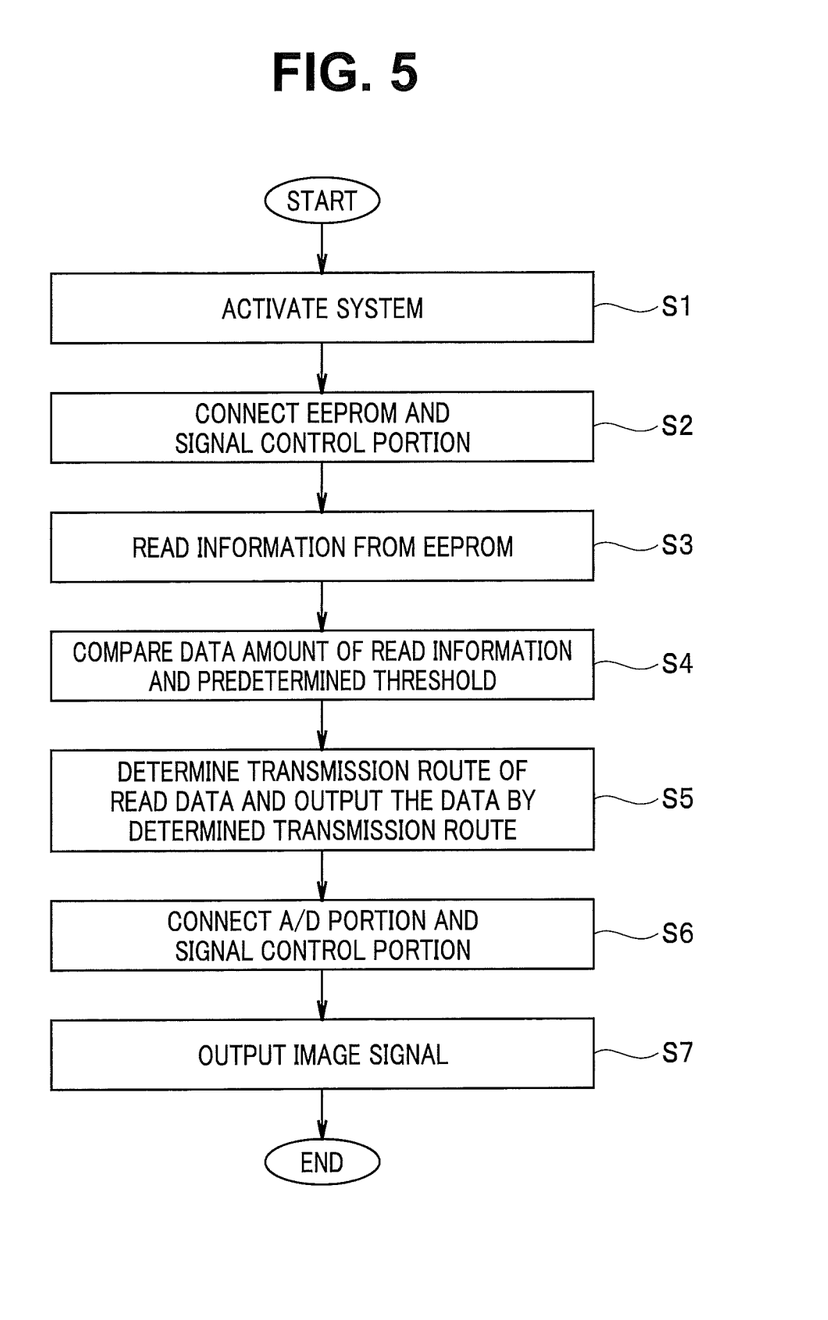
FIG. 5 is a flowchart illustrating an operation of a signal control portion 42 relating to the embodiment of the present invention.

FIG. 5 is a flowchart illustrating an operation of the signal control portion 42. FIG. 5 illustrates an example of a flow of processing when the endoscope 2 is connected to the video processor 3 and the endoscope system 1 is activated.

When the endoscope system 1 is activated (S1), the determination control portion 42a controls the data switching portion 41 so as to connect the EEPROM 28 and the signal control portion 42 (S2). More specifically, the connection state of the input ends and the output ends inside the data switching portion 41 is switched so as to connect the output end O1 of the switch SW1 and the input end I3 of the EEPROM 28.

Next, the determination control portion 42a outputs a data read signal RC to the EEPROM 28, and reads the information stored in the EEPROM 28, the information concerning the image processing in this case, from the EEPROM 28 through the data switching portion 41 (S3).

That is, the signal control portion 42 starts reading of the predetermined information from the EEPROM 28 based on activation of the power supply circuit 35 which is the power supply portion.

The determination control portion 42a can recognize the data amount of the information when reading the information stored in the EEPROM 28. Therefore, the determination control portion 42a compares the data amount of the read information and the predetermined threshold TH (S4).

The determination control portion 42a determines whether or not the data amount of the information read from the EEPROM 28 is equal to or larger than the predetermined threshold TH from a comparison result in S4, decides a transmission route of the read data based on the determination result, and outputs the read data to the decided transmission route (S5).

More specifically, in the case where the data amount of the information read from the EEPROM 28 is smaller than the predetermined threshold TH, the determination control portion 42a selects the one wire 5b1a of the plurality of wires 5b as the transmission route. For example, in the case where the read information is the ID or the defective pixel information of a small data amount, the electric wire is selected as the transmission route, and the information is transmitted to the video processor 3 by the wire.

In addition, in the case where the data amount of the information read from the EEPROM 28 is equal to or larger than the predetermined threshold TH, the determination control portion 42a selects an optical fiber 5a1 of the two optical fibers 5a of the electro-optical conversion portion 27 as the transmission route. For example, in the case where the read information is the image processing program of a large data amount, the optical fiber is selected as the transmission route, and the information is transmitted to the video processor 3 by the optical fiber.

As above, the determination control portion 42a decides through which of the metal transmitting member and the optical transmitting member the information read from the EEPROM 28 is to be transmitted, based on the data amount of the information read from the EEPROM 28. Then, when the data amount of the information read from the EEPROM 28 is equal to or larger than a predetermined value, the determination control portion 42a controls the data switching portion 41 so as to transmit the information read from the EEPROM 28 through the optical transmitting member.

The information read from the EEPROM 28 is converted to the serial signals in the P/S 42b, and then outputted by the decided transmission route.

When the information is the image processing program of a large data amount for example, since the information is transmitted quickly by optical transmission, the transmission of the image signals can be quickly started.

After reading of the information from the EEPROM 28 and the sending to the video processor 3, the determination control portion 42a controls the data switching portion 41 so as to connect the A/D 23 and the signal control portion 42 (S6). More specifically, as illustrated by a two-dot chain line in FIG. 4, the connection state of the input ends and the output ends inside the data switching portion 41 is switched so as to connect the input end I1 and the output end O1 of the switch SW1 and connect the input end I2 and the output end O2 of the switch SW2.

After switching the connection state of the data switching portion 41, the determination control portion 42a sends a control signal SS to the control circuit 25 of the image pickup device 14 so as to output the two image signals, and outputs the two image signals to the electro-optical conversion portion 27 (S7). The two image signals are converted to the serial signals in the P/S 42b and then outputted to the electro-optical conversion portion 27.

As described above, in the present embodiment, the universal cable 5 is the cable configured by the plurality (two, here) of optical transmitting members configured to transmit the optical signals outputted from each electro-optical conversion portion and the metal transmitting members configured to transmit the data outputted from the signal control portion 42. The signal control portion 42 selectively converts the data of at least one of the digital signal which is the image signal outputted from the image pickup device 14 and the information read from the EEPROM 28 to serial data and outputs the serial data. The data switching portion 41 is switched so as to transfer the information read from the EEPROM 28 to the video processor 3 by the signal control portion 42 and then transfer the digital signal to the video processor 3 by the signal control portion.

Note that, in the example described above, the information is transmitted by the wire when the data amount of the information in the EEPROM 28 is small. However, the information may be transmitted by the optical fiber.

As above, according to the embodiment described above, after the information concerning the image processing is transmitted to the video processor 3, the two image signals of the two pixel areas 21a and 21b are transmitted to the video processor 3.

As a result, not only the image processing is appropriately performed but also the image processing can be quickly executed.

Note that, in the example described above, the image signals are transmitted to the video processor 3 by the optical fiber selected as the transmission route. However, when the optical fiber is abnormal, the wire may be selected as the transmission route and the image signals may be transmitted to the video processor 3 by the electric wire.

Thus, according to the embodiment described above, it is possible to provide the endoscope system and the endoscope capable of appropriately transmitting the information concerning the image processing of the image signal to the processor, in the endoscope system that transmits the image signal by the optical signal.

Note that, in the embodiment described above, the endoscope is a rigid endoscope. However, the endoscope may be a flexible endoscope, the insertion portion of which is flexible.

The present invention is not limited to the embodiment described above, and various changes and modifications or the like are possible without changing a subject matter of the present invention.

What is claimed is:

1. An endoscope system comprising:
   an image sensor configured to pick up an image inside a subject and to output a digital signal;
   a memory configured to record predetermined information concerning an endoscope;
   a signal controller configured to selectively convert data of one of the digital signal outputted from the image sensor and the predetermined information in the memory to serial data and outputting the serial data;
   an electro-optical converter configured to convert the data outputted from the signal controller to an optical signal and to output the optical signal;
   a cable comprising an optical transmitting member configured to transmit the optical signal outputted from the electro-optical converter and a metal transmitting member configured to transmit the data outputted from the signal controller; and
   a data switch configured to switch between transferring the predetermined information from the memory to the signal controller and transferring the digital signal from the image sensor to the signal controller,
   wherein the signal controller is further configured to decide through which of the metal transmitting member and the optical transmitting member the predetermined information is transmitted, based on a data amount of the predetermined information.

2. The endoscope system according to claim 1, wherein the signal controller is further configured to control the data switch to transmit the predetermined information through the optical transmitting member when the data amount of the predetermined information is equal to or larger than a predetermined value.

3. The endoscope system according to claim 1, further comprising an opto-electrical converter configured to convert the optical signal transmitted by the optical transmitting member to an electric signal.

4. The endoscope system according to claim 3, wherein the opto-electrical converter is provided around a connector at an end portion of the cable.

5. The endoscope system according to claim 1, further comprising an image processor configured to execute image processing on the digital signal based on the predetermined information, and generate an endoscopic image.

6. The endoscope system according to claim 1, wherein the predetermined information recorded inside the memory includes at least one of endoscope scope information, a serial number of a camera head, pixel defect information of the image sensor, white balance information, color variation correction information and an image processing program.

7. The endoscope system according to claim 1, wherein
   the optical transmitting member comprises a plurality of optical transmitting members, and
   a number of the optical transmitting members provided in parallel inside the cable is equal to a number of image signals simultaneously outputted from the image sensor and separately transmitted in parallel to a respective one of the plurality of optical transmitting members.

8. The endoscope system according to claim 1, wherein the image sensor, the electro-optical converter, the memory and the signal controller are provided inside a camera head.

9. The endoscope system according to claim 8, further comprising a power supply inside the camera head,
   wherein the signal controller is configured to start reading the predetermined information from the memory based on activation of the power supply.

10. An endoscope comprising:
    an image sensor configured to pick up an image inside a subject and to output a digital signal;
    a memory configured to record predetermined information concerning the endoscope;
    a signal controller configured to selectively convert data of one of the digital signal outputted from the image sensor and the predetermined information in the memory to serial data and outputting the serial data;
    an electro-optical converter configured to convert the data outputted from the signal controller to an optical signal and to output the optical signal; and
    a data switch configured to switch between transferring the predetermined information from the memory to the signal controller and transferring the digital signal from the image sensor to the signal control portion,
    wherein the signal controller is further configured to decide through which of a metal transmitting member and an optical transmitting member the predetermined information is transmitted, based on a data amount of the predetermined information.

* * * * *